United States Patent [19]

Yamauchi

[11] Patent Number: 4,920,956
[45] Date of Patent: May 1, 1990

[54] ACUPRESSURE TYPE RHINITIS THERAPEUTIC DEVICE

[76] Inventor: Shouji Yamauchi, 3-7, Chuo-cho, Sohara, Kagamigahara-shi, Gifu-ken, Japan

[21] Appl. No.: 237,532

[22] Filed: Aug. 29, 1988

[30] Foreign Application Priority Data

Aug. 31, 1987 [JP] Japan .................... 62-133087[U]

[51] Int. Cl.⁵ .............................................. A61F 7/00
[52] U.S. Cl. .................... 128/24.1; 128/399
[58] Field of Search .................... 128/24.1, 67, 60, 61, 128/59, 64, 54, 907, 300, 399, 403

[56] References Cited

U.S. PATENT DOCUMENTS

| | | | |
|---|---|---|---|
| 1,380,986 | 6/1921 | Linden | 128/60 |
| 1,456,452 | 5/1923 | Linden | 128/60 |
| 1,795,893 | 3/1931 | Rosett | 128/64 |
| 2,299,162 | 10/1942 | Marick | 128/399 |
| 2,469,771 | 5/1949 | Jeppson | 128/24.1 |
| 2,635,175 | 4/1953 | Hodge | 128/399 |
| 2,836,175 | 5/1958 | Nakayama | 128/60 |
| 3,028,857 | 4/1962 | Parker | 128/67 |
| 3,159,160 | 12/1964 | Ullom | 128/403 |
| 3,411,498 | 11/1968 | Reiter | 128/57 |
| 4,034,787 | 7/1977 | Ellis | 128/380 |
| 4,233,966 | 11/1980 | Takahashi | 128/67 |
| 4,463,485 | 8/1984 | Gueret | 128/67 |
| 4,550,718 | 11/1985 | Kaeser | 128/57 |
| 4,554,911 | 11/1985 | Nielsen | 128/57 |
| 4,574,787 | 3/1986 | Jacobs | 128/380 |
| 4,614,189 | 9/1986 | Mackenzie | 128/380 |

FOREIGN PATENT DOCUMENTS

| | | | |
|---|---|---|---|
| 344528 | 11/1921 | Fed. Rep. of Germany | 128/60 |
| 348491 | 2/1922 | Fed. Rep. of Germany | 128/57 |
| 61-18121 | 1/1986 | Japan . | |

OTHER PUBLICATIONS

"Acu-Hood", from What the World Needs Now by Steven M. Johnson, ©1984, p. 26.

Primary Examiner—Edgar S. Burr
Assistant Examiner—Tonya Lamb
Attorney, Agent, or Firm—Oliff & Berridge

[57] ABSTRACT

An acupressure type rhinitis therapeutic device has at least three heat transfer acupressure members for transferring thermal stimulus from a heat source to a first acupressure point at the center of a glabella and to second acupressure points at opposite bottom sides of a nasal bone which are all effective acupoints in rhinitis therapy, which permits a user to obtain improved nasal blood circulation. A fire is not required as opposed to moxibution so that rhinitis can easily and safely be treated even at home. Further, there is little difference in the positions of the first and second acupressure points among individuals so that the rhinitis therapeutic device can be mass-produced.

33 Claims, 12 Drawing Sheets

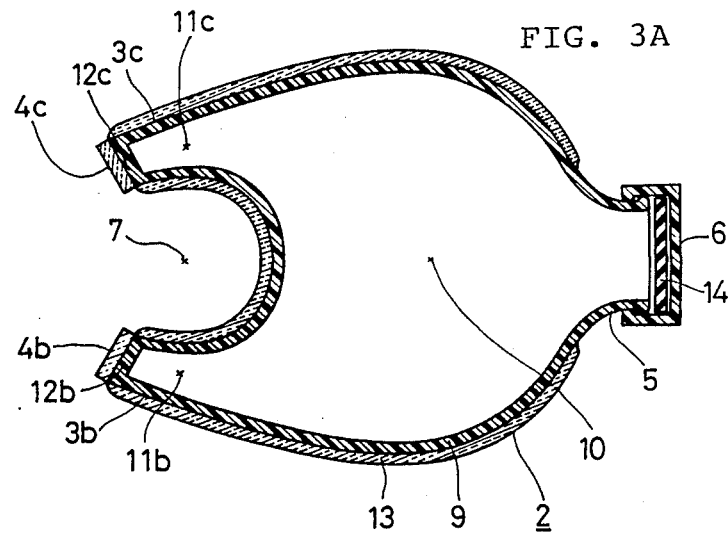
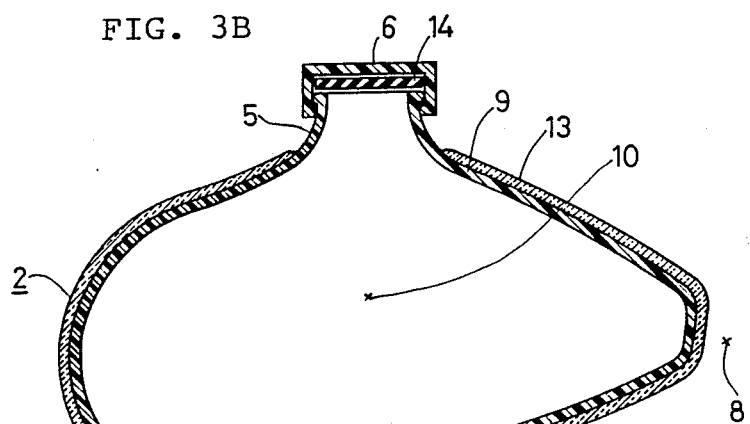
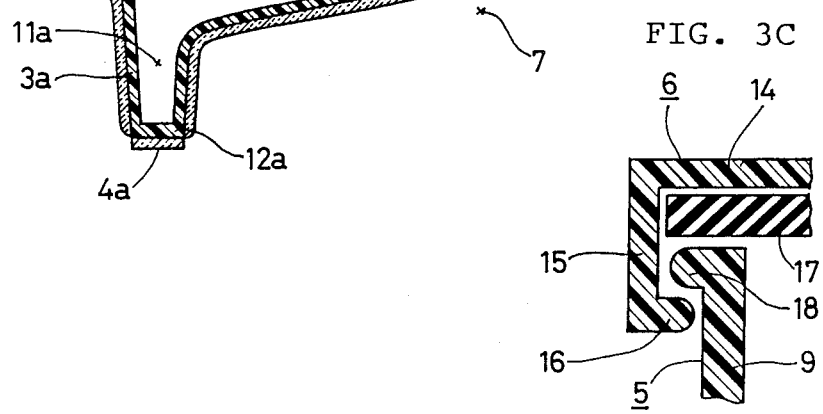

ACUPRESSURE TYPE RHINITIS THERAPEUTIC DEVICE

BACKGROUND OF THE INVENTION

The present invention relates to a rhinitis therapeutic device, and in particular, to an acupressure type rhinitis therapeutic device for giving thermal stimulus as rhinitis therapy to some acupoints of a human face.

Prior to the present invention, there is a method for a rhinitis therapy in which a nasal vessel is contracted by use of collunarium so that a nasal cavity may be enlarged for easier nasal air flow. The collunarium has a big transient effect, however, an overuse of the collunarium increases the fastness of the nasal vessel, leading to reduced therapeutic effect. Therefore, the collurarium is preferably used only for transient rhinitis such as cold. Further, Published Unexamined Utility Model No. 61-18121 discloses a rhinitis therapeutic device for warming an area from nasal sides to a cheek by use of a heating unit. However, the rhinitis therapeutic device does not stimulate acupoints for effective rhinitis therapy which exist from a glabella to opposite bottom sides of a nasal bone, resulting in reduced effectiveness of the stimulus.

SUMMARY OF THE INVENTION

It is an object of the invention is to provide an acupressure type rhinitis therapeutic device which can supply thermal stimulus and acupressure to at least three acupoints of a human face effective for rhinitis therapy for improving nasal blood circulation.

It is another object of the invention to provide an acupressure type rhinitis therapeutic device which can be mass-produced.

It is a further object of the invention to provide an acupressure type rhinitis therapeutic device that can easily and safely be used at home.

The foregoing objects will be attained by providing an acupressure type rhinitis therapeutic device for giving thermal stimulus to a first acupressure point at a center of a glabella and to a pair of second acupressure points at opposite bottom sides of a nasal bone, the acupressure type rhinitis therapeutic device comprising: a body having a first acupressure member (3a, 23a, and 43a) contactable with said first acupressure point and second acupressure members (3b, 3c, 23b, 23c, 43b and 43c) contactable with said second acupressure points; and a means for warming the three acupressure members (3a, 3b, 3c, 23a, 23b, 23c, 43a, 43b and 43c).

BRIEF DESCRIPTION OF THE DRAWINGS

Other objects and features of the invention will become apparent to those skilled in the art as the disclosure is made in the following invention, as illustrated in the accompanying drawings:

FIG. 3A is a sectional view taken on line IIIA—IIIA of FIG. 2D;

FIG. 3B is a sectional view taken on line IIIB—IIIB of FIG. 2D;

FIG. 3C is a enlarged sectional view of the vicinity of a cap to better illustrate the construction thereof;

DETAILED DESCRIPTION OF THE PREFERRED EMBODIMENT

Hereinafter, preferred embodiments of the present invention will be described in detail with reference to the drawings.

Figure 1:
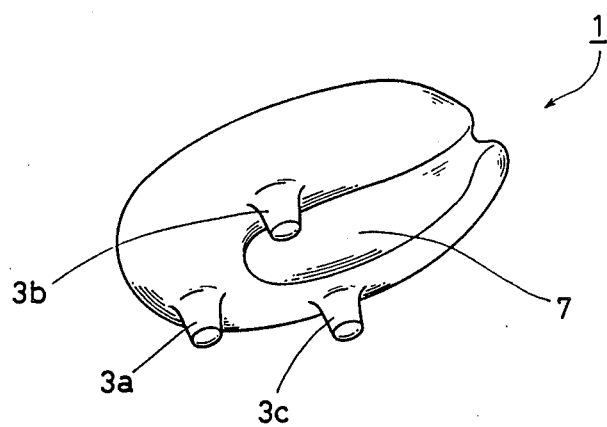
FIG. 1 is a perspective view of a hot water rhinitis therapeutic device seen from a rear bottom side thereof as a first embodiment of the present invention.
Figure 2A:
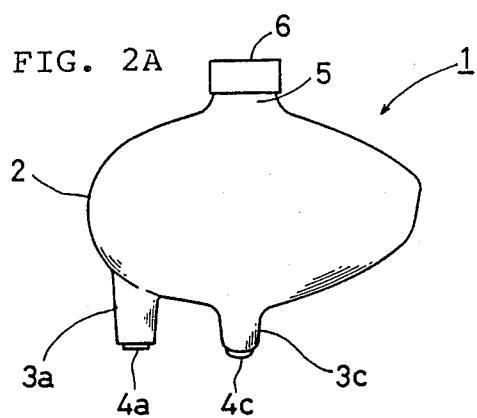
FIG. 2A is a side view of the hot water rhinitis therapeutic device.
Figure 2B:
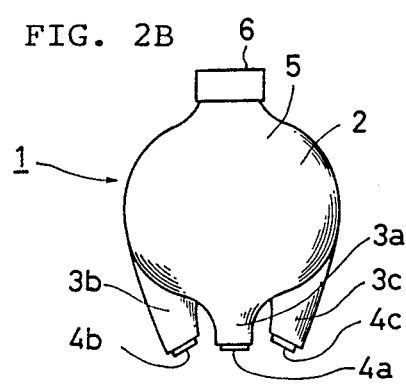
FIG. 2B is a front view of the hot water rhinitis therapeutic device.
Figure 2C:
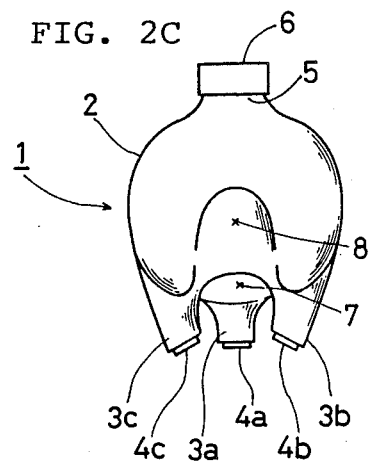
FIG. 2C is a rear view of the hot water rhinitis therapeutic device.
Figure 2D:
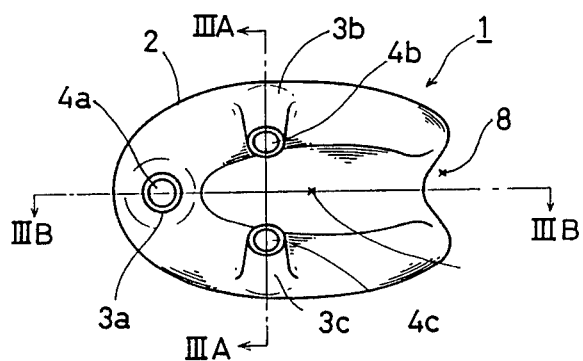
FIG. 2D is a bottom view of the hot water rhinitis therapeutic device.

Referring now to FIG. 1, there is shown a hot water rhinitis therapeutic device 1 of a first embodiment which includes a cylindrical straight first acupressure projection 3a and a pair of cylindrical curved second acupressure projections 3b and 3c on an underside thereof corresponding to a first acupressure point at the center of a glabella and second acupressure points at opposite bottom sides of a nasal bone, respectively. The hot water rhinitis therapeutic device 1, further, includes a recess 7 on the underside thereof for holding the hot water rhinitis therapeutic device 1 away from a bridge of a nose so that only the acupressure projections 3a, 3b and 3c may touch a human face during rhinitis therapy.

As shown in FIGS. 2A through 2D, the hot water rhinitis therapeutic device 1 also includes an egg-shaped tank 2 for containing hot water therein as a heat source. The recess 7 gradually deepens from a point slightly to the rear of the first acupressure projection 3a as it extends to a rear end along a line IIIB—IIIB which is a longitudinal center line of the hot water rhinitis therapeutic device 1. The first acupressure projection 3a lies on the line IIIB—IIIB and the acupressure projections 3b and 3c are disposed oppositely to each other on the contour line of the recess 7. A recess 8 is formed at the rear end of the tank 2 for a user to easily hold the hot water rhinitis therapeutic device 1 with his fingers during the rhinitis therapy. The recesses 7 and 8 are continuously integrated.

As shown in FIG. 3B, a top surface of the first acupressure projection 3a which is substantially perpendicular thereto is covered with a round heat transfer plate 12a of a predetermined thickness onto which a felt 4a is adhered. Further, as shown in FIG. 3A, the top surfaces of the second acupressure projections 3b and 3c which are oblique thereto are covered with round transfer plates 12b and 12c of a predetermined thickness onto which felts 4b and 4c are adhered. The heat transfer plates 12a, 12b and 12c are integrated with a wall 9 of a predetermined thickness. The second acupressure projections 3b and 3c can accurately grip the second acupressure points at the opposite bottom sides of the nasal bone with the help of the oblique top surfaces thereof.

The wall 9 of the tank 2 includes a cylindrical filling port 5 at a center top portion thereof which has a cap 6 for avoiding leakage of the hot water, and a main chamber 10 for containing the hot water therein. The first and second acupressure projections 3a, 3b and 3c include heat transfer chambers 11a, 11b and 11c therein, respectively. The main chamber 10 and the heat transfer chambers 11a, 11b and 11c are continuously integrated. The hot water is introduced through the filling port 5 into the main chamber 10 and then into the heat transfer chambers 11a, 11b and 11c, with the result that heat is transferred to the felts 4a, 4b and 4c via the heat transfer plates 12a, 12b and 12c, respectively. The wall 9 except the filling port 5 and the heat transfer plates 12a, 12b and 12c is covered with a heat insulator 13, thereby preventing the heat from leaking out therefrom.

As shown in FIG. 3C, the cap 6 designed for closing the filling port 5 includes a round roof plate 14, and a cylindrical side plate 15 which extends vertically down from the roof plate 14. At a lower edge of the side plate 15, a stopper ring 16 which projects horizontally and inwardly is provided. A resilient packing 17 of a predetermined thickness is fitted between the roof plate 14 and the stopper ring 16. A ring flange 18 projects horizontally and outwardly from one upper of the filling port 5. A diameter of the flange 18 is less than an inner diameter of the side plate 15 but greater than an inner diameter of the stopper ring 16. When the filling port 5 is covered with the cap 6, the packing 17 is pushed by an upper surface of the flange 18 and a lower surface of the roof plate 1 4 and held therebetween. At the same time, a lower surface of the flange 18 and an upper surface of the stopper ring 16 are pushed together due to the resilience of the packing 17 to seal the filling port 5 of the tank 2.

Figure 4A:
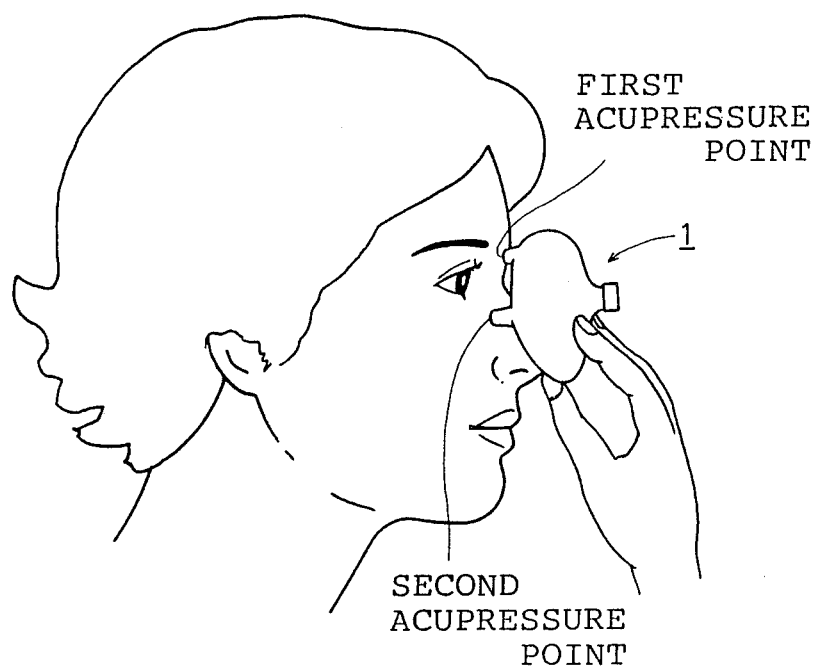
FIG. 4A is a side view of the hot water rhinitis therapeutic device in use.
Figure 4B:
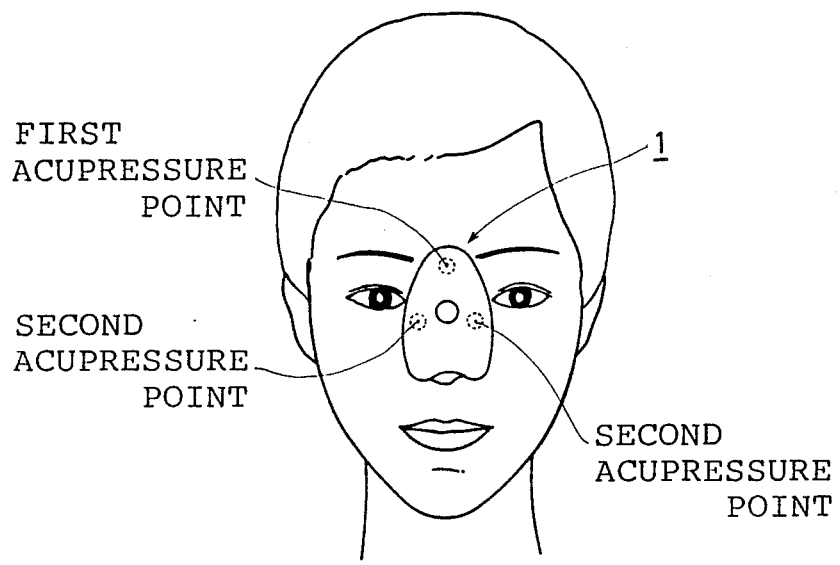
FIG. 4B is a front view of the hot water rhinitis therapeutic device in use.

As shown in FIGS. 4A and 4B, the first and second acupressure projections 3a, 3b and 3c of the hot water rhinitis therapeutic device 1 which contains the hot water therein as the heat source are respectively applied to the first and second acupressure points for supplying thermal stimulus thereto. When the respective felts 4a, 4b and 4c of the first and second acupressure projections 3a, 3b and 3c are moistened by water, a hot compress effect as well as a thermal stimulus effect can be obtained, resulting in a more effective rhinitis therapy. Further, when the felts 4a, 4b and 4c are moistened by garlic juice, ginger juice, mugwort juice or such, an effect of medicinal components included in garlic, ginger, mugwort and such as well as the thermal stimulus effect can be obtained. In other words, an effect similar to garlic moxibution, ginger moxibution, mugwort moxibution and the like performed by an acupuncture and moxibution doctor can be obtained. Moreover, the intensity of the thermal stimulus can be changed by controlling the applied pressure onto three acupressure points through the hot water rhinitis therapeutic device 1, and water temperature are moderated to adjust the intensity of the thermal stimulus so that a desired thermal stimulus may be obtained for the rhinitis therapy.

As above-mentioned, in the first embodiment of the present invention, the first and second acupressure points are adopted as effective rhinitis therapy because all of them exist near the nasal bone, and there is little difference in the positions of those acupoints among individuals. Therefore, only three models of rhinitis therapeutic devices (such as infant's, woman's and man's) are necessary to produce with the result that production costs thereof are reduced and applicability is wider. Moreover, the hot water is used as the heat source so that the desired thermal stimulus can be obtained by moderating the temperature of the hot water, and also there is no risk of a fire during the therapy. Furthermore, no special skill for stimulating the acupoints is necessary so that the rhinitis can easily and safely be treated even at home.

Described below is a second embodiment of the present invention.

Figure 5:
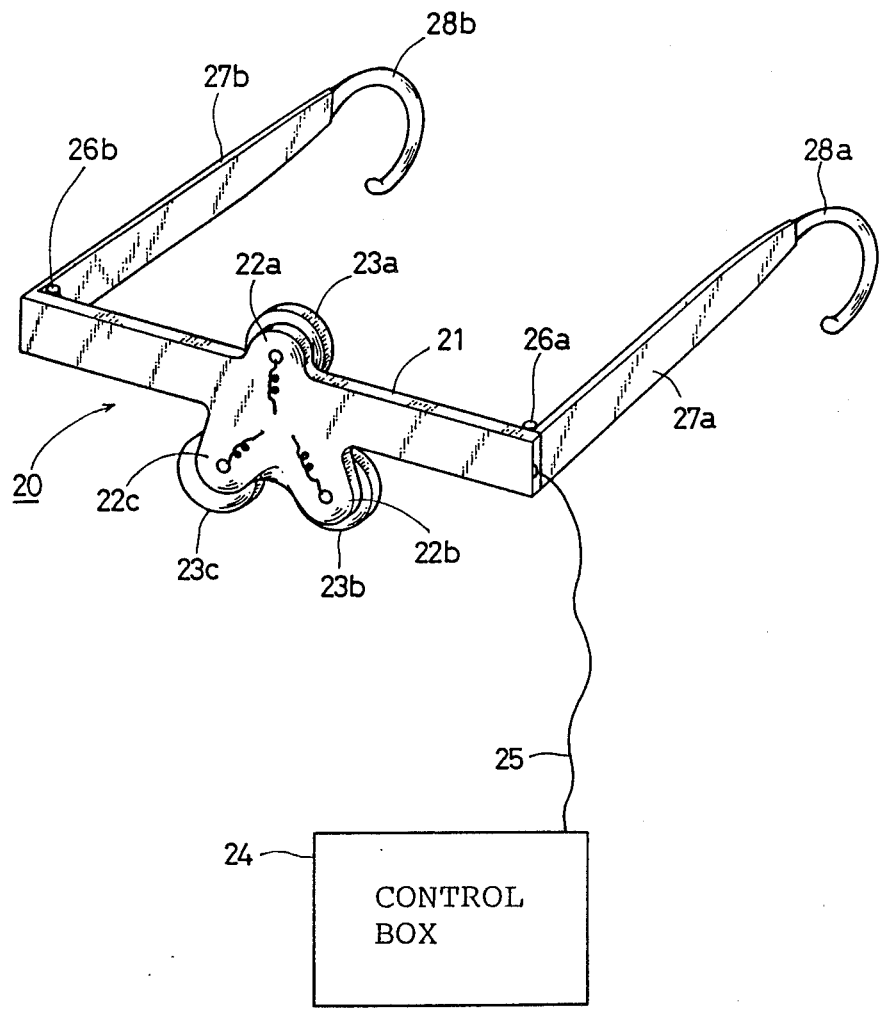
FIG. 5 is a perspective view of a ceramic heater rhinitis therapeutic device as a second embodiment of the present invention.
Figure 7A:
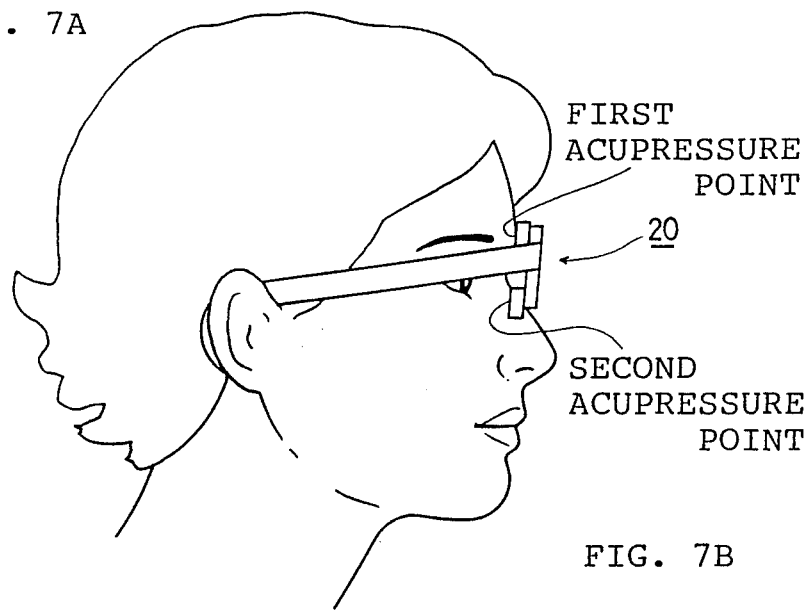
FIG. 7A is a side view of the ceramic heater rhinitis therapeutic device in use.
Figure 7B:
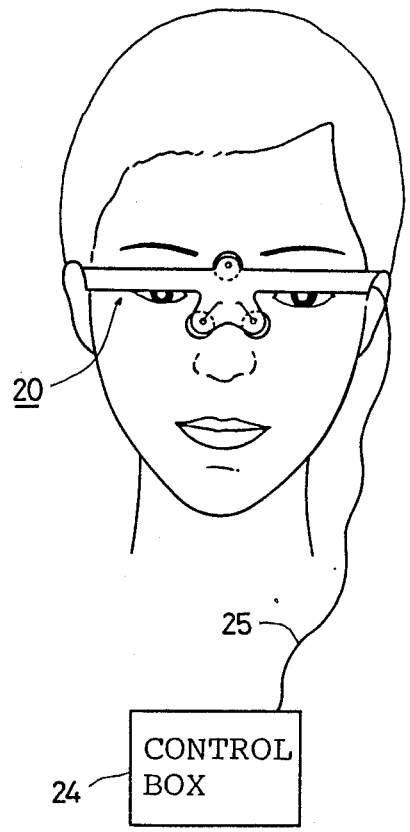
FIG. 7B is a front view of the ceramic heater rhinitis therapeutic device in use.

As shown in FIG. 5, a glasses-frame like ceramic heater rhinitis therapeutic device 20 includes a straight front bar 21. The front bar 21 has a projection 22a which projects upwardly from the center thereof, and a pair of projections 22b and 22c which project downwardly and diagonally in the opposite directions from the center thereof. The respective projections 22a, 22b and 22c have heat transfer acupressure members 23a, 23b and 23c in the reverse sides thereof, which correspond to the first acupressure point and the second acupressure points, respectively. A pair of temples 27a and 27b are connected to opposite ends of the front bar 21 by hinges 26a and 26b, respectively, and a pair of resilient end pieces 28a and 28b are fixed to the pair of temples 27a and 27b, respectively. The pair of temples 27a and 27b can pivot at the hinges 26a and 26b so that they can fold up along the front bar 21, respectively when the ceramic heater rhinitis therapeutic device 20 is not in use. On the other hand, as shown in FIGS. 7A and 7B, when the ceramic heater rhinitis therapeutic device 20 is in use, the end pieces 28a and 28b worn around the ears push the front bar 21 to a human face with the help of resilience thereof. Further, the ceramic heater rhinitis therapeutic device 20 includes an external control box 24 for charging an electric power thereto. The control box 24 is connected to the ceramic heater rhinitis therapy device 20 via a cord 25 which is provided at one end of the front bar 21.

Figure 6A:
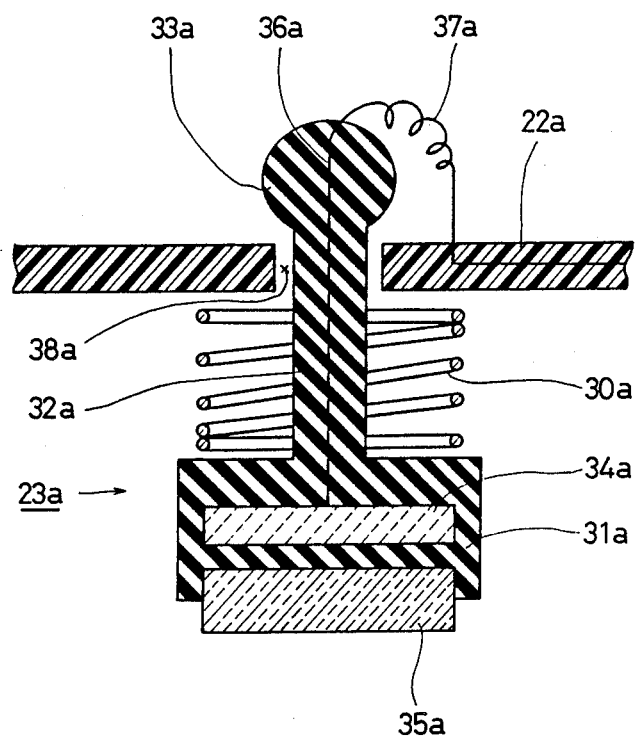
FIG. 6A is a sectional view of the vicinity of a heat transfer acupressure member to better illustrate the construction thereof.
Figure 6B:
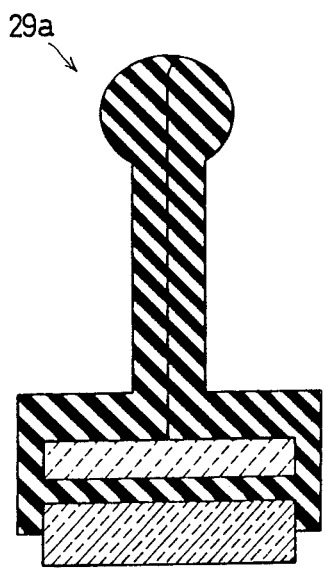
FIG. 6B is a sectional view of an acupressure member of the heat transfer acupressure member.

Referring to FIGS. 6A and 6B, the heat transfer acupressure member 23a is explained in detail. The explanation about the heat transfer acupressure members 23b and 23c is omitted since they have the same construction as the heat transfer acupressure member 23a.

The heat transfer acupressure member 23a includes an acupressure member 29a made of an electric insulator, and a coil spring 30a. The acupressure member 29a has a thick and round plate-like heating unit 31a on a lower portion thereof. A round support rod 32a upwardly projects from the center of an upper surface of the heating unit 31a, and at the top of the support rod 32a, is provided an engaging ball 33a. A ceramic heater 34a is provided in the heating unit 31a as the heat source and is heated by the electric power charged from the control box 24 via the cord 25. Further, a felt 35a is fitted into a bottom portion of the heating unit 31a. A predetermined interval is kept between the ceramic heater 34a and the felt 35a by the electric insulator of which the heating unit 31a is made. A lead wire 36a runs from the ceramic heater 34a through the support rod 32a and the engaging ball 33a to the outside, and on into the projection 22a of the front bar 21 to join with the cord 25. In addition, the lead wire 36a has an elastic coil 37a between the engaging ball 33a and the projection 22a.

The projection 22a has a hole 38a into which the heat transfer acupressure member 23a is inserted. The engaging ball 33a is larger in diameter by a predetermined size than the hole 38a to prevent the heat transfer acupressure member 23a from dropping therefrom. The coil spring 30a is provided between the projection 22a and the heating unit 31a around the support rod 32a to push the felt 35a of the acupressure member 29a against the human face when the ceramic heater rhinitis therapeutic device 20 is in use. Further, the hole 38a is larger in diameter by a predetermined size than the support rod 32a so that the heat transfer acupressure member 23a may flexibly tilt in accordance with a contour of the human face to accurately press against the acupoint. The heat from the ceramic heater 34a is transferred to the felt 35a via the heating unit 31a.

Still further, in the ceramic heater rhinitis therapeutic device 20 of the second embodiment, the electric power loaded to the ceramic heater 34a is controlled by the control box 24 to adjust the intensity of the thermal stimulus. In a similar way to the first embodiment, when the felt 35a is moistened by water, the hot compress effect as well as the thermal stimulus effect can be obtained. On the other hand, when the felt 35a is moistened by garlic juice, ginger juice, mugwort juice or such in place of water, the effect of the medical components thereof as well as the hot compress effect can be obtained. If the control box 24 is portable, the user can do routine work, have a meal and so on during the rhinitis therapy. In addition, since there is little individual difference regarding the positions of the first and second acupressure points, the ceramic rhinitis therapeutic device 20 can be mass-produced.

Figure 8:
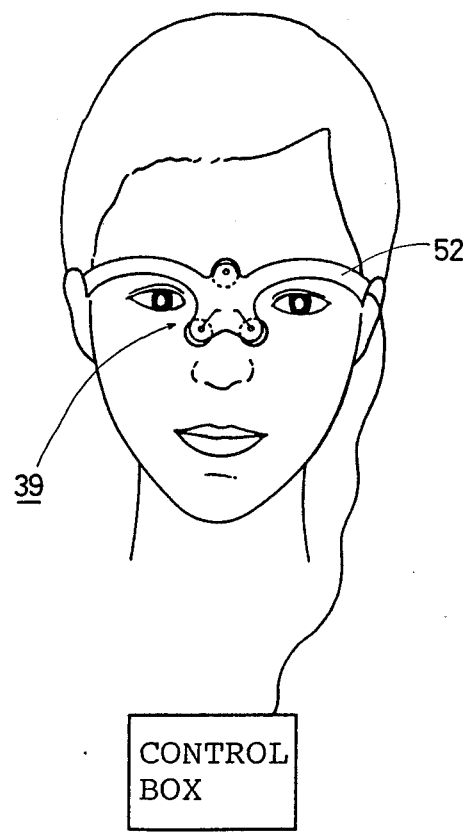
FIG. 8 is a front view of a ceramic heater rhinitis therapeutic device in use as a third embodiment of the present invention.
Figure 9A:
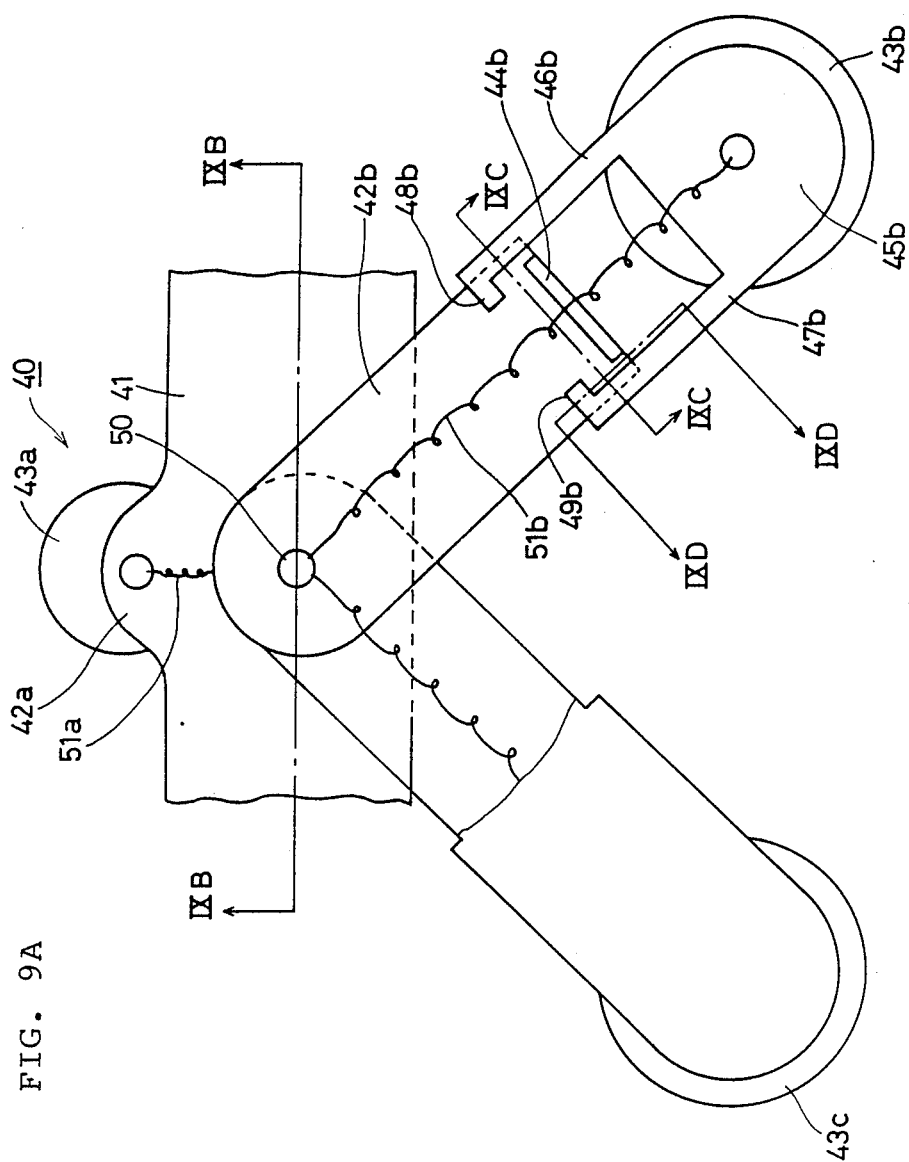
FIG. 9A is a front view of a ceramic heater rhinitis therapeutic device as a fourth embodiment of the present invention to better illustrate the characteristic construction thereof.
Figure 9B:
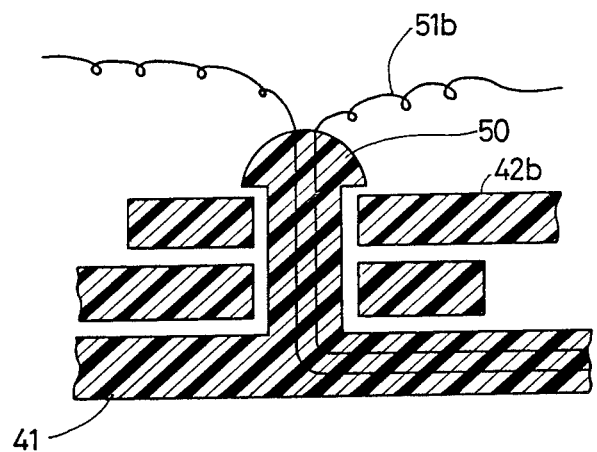
FIG. 9B is a sectional view taken on line IXB—IXB of FIG. 9A.
Figure 9C:
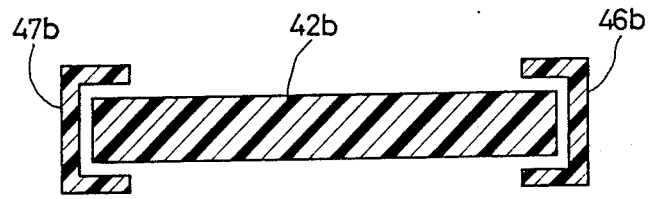
FIG. 9C is a sectional view taken on line IXC—IXC of FIG. 9A.
Figure 9D:
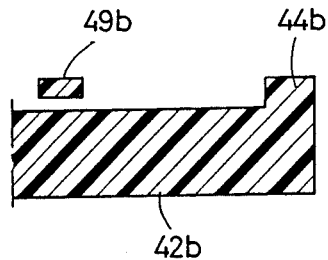
FIG. 9D is a sectional view taken on line IXD—IXD of FIG. 9A.
Figure 10:
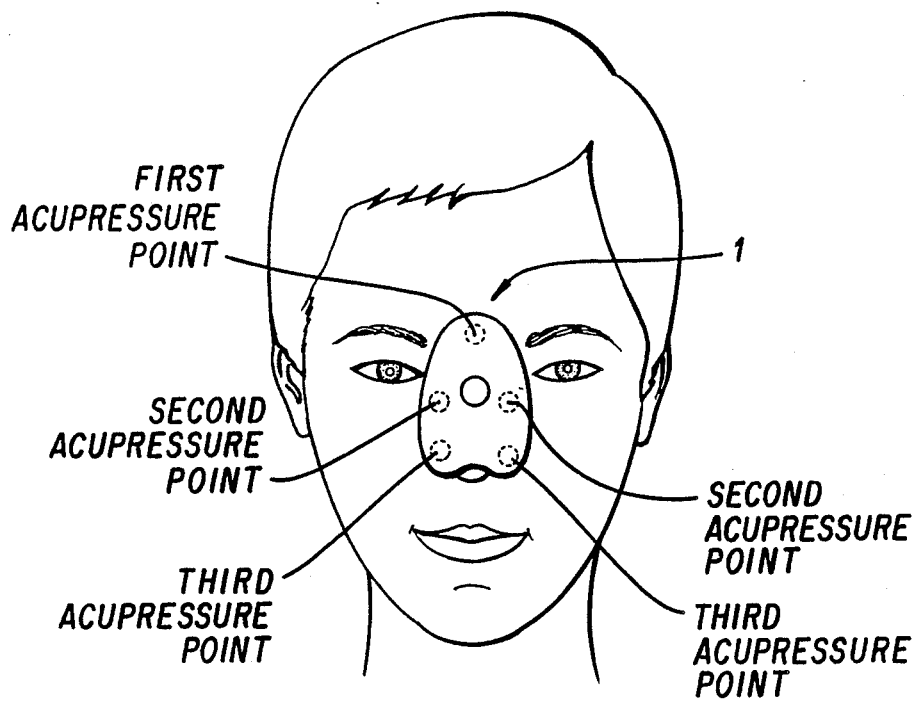
FIG. 10 is a front view of a fifth embodiment of the hot water rhinitis therapeutic device in use.

Explained next is a third embodiment of the present invention with reference to FIG. 8.

A ceramic heater rhinitis therapeutic device 39 has the same construction as the second embodiment except for a front bar 52. The front bar 52 is curved along eyebrows for a good view, thereby allowing the user to be more active.

Described hereinafter is a fourth embodiment of the present invention with reference to FIGS. 9A through 9D.

A ceramic heater rhinitis therapeutic device 40 has the same construction as the second embodiment except for a pair of heat transfer acupressure members 43b and 43c corresponding to the second acupressure points. The pair of heat transfer acupressure members 43b and 43c can be moved right or left, and up or down so as to more accurately press the second acupressure points, although there is little individual difference in the location of the second acupressure points.

Since the heat transfer acupressure members 43b and 43c have the same construction, the heat transfer acupressure member 43b is taken for a more detailed description. A front bar 41 includes a projection 42a for fixing thereon a heat transfer acupressure member 43a corresponding to the first acupressure point and a rivet pin 50 in the center thereof for supporting a pivotable piece 42b. The heat transfer acupressure member 43b is provided on a sliding support frame 45b similarly to the second embodiment which has been explained with reference to FIGS. 6A and 6B, and is connected to the pivotable piece 42b via the sliding support frame 45b. A stopper 44b forwardly projects from a lower edge of the pivotable piece 42b. A lead wire 51a is led from the heat transfer acupressure member 43a directly into the front bar 41, while a lead wire 51b is led from the heat transfer acupressure member 43b via the top of the rivet pin 50 to the inside of the front bar 41. The sliding support frame 45b has a channel-shaped sliding rail 46b engaging with the pivotable piece 42b on a right upper portion thereof and a channel-shaped sliding rail 47b on a left upper portion thereof. The sliding rails 46b and 47b have projections 48b and 49b on upper edges thereof, respectively, which project toward the center of the pivotable piece 42b. The stopper 44b and the projections 48b and 49b prevent the sliding support frame 45b having the heat transfer acupressure member 43b from dropping from the pivotable piece 42b.

In the fourth embodiment constructed above, a position of the heat transfer acupressure member 43b corresponding to the second acupressure point is flexibly adjustable right or left, and up or down so that rhinitis therapy for every patient such as infants, women and men can be performed with only one model of the device.

Obviously, many modifications and variations of the present invention are possible as pointed out with regard to the above revelations. It is therefore to be understood that within the scope of the appended claims, the invention may be practiced otherwise than as specifically described.

For example, the first and second acupressure projections 3a, 3b and 3c in the first embodiment may be solid-type made of material having a high efficiency of heat transfer, such as bronze, instead of hollow cylinder-type. Further, the cap 6 may be replaced with a screw-type cap or a cork. Still further, in these embodiments of the present invention, in view of merits for producing the rhinitis therapeutic devices, the first and second acupressure points are adopted as the acupoints to be stimulated, however, there are two other acupoints effective for the rhinitis therapy at opposite sides of wings of the nose. Therefore, the rhinitis therapeutic device of the present invention can provide five heat transfer acupressure members corresponding to as many acupoints effective for rhinitis therapy.

What is claimed is:

1. An acupressure type rhinitis therapeutic device for giving thermal stimulus to a first acupressure point at a center of a glabella and to a pair of second acupressure points at opposite bottom sides of a nasal bone, said acupressure type rhinitis therapeutic device comprising:
   a body having only three acupressure members, consisting of a first acupressure member contactable with said first acupressure point and a pair of second acupressure members contactable with said second acupressure points; and
   a means for warming said three acupressure members.

2. An acupressure type rhinitis therapeutic device according to claim 1, wherein said means for warming said three acupressure members is a hot fluid contained in said tank.

3. An acupressure rhinitis therapeutic device according to claim 1, wherein said means for warming said three acupressure members is an elastic coils inserted into said three acupressure members, respectively.

4. An acupressure type rhinitis therapeutic device according to claim 1, wherein said second acupressure members can move right or left, and up or down so as to more accurately press said second acupressure points, although there is little difference in location of said second acupressure points among individuals.

5. An acupressure type rhinitis therapeutic device according to claim 1, wherein said body is a tank for containing hot fluid therein, and said acupressure members are integrally connected to an underside of said tank and project downwardly therefrom.

6. An acupressure type rhinitis therapeutic device according to claim 5, wherein said tank includes a main chamber for containing said hot fluid therein, and said three acupressure members include heat transfer chambers therein, respectively, said main chamber and said heat transfer chambers being continuously integrated.

7. An acupressure rhinitis therapeutic device according to claim 1, wherein said body is a front bar of a glasses-frame like ceramic heater rhinitis therapeutic device.

8. An acupressure type rhinitis therapeutic device according to claim 7, wherein said front bar is curved along eyebrows.

9. An acupressure type rhinitis therapeutic device according to claim 7, wherein said front bar includes a projection for fixing thereon said first acupressure member corresponding to said first acupressure point and a rivet pin in a center thereof for fixing a pivotable piece.

10. An acupressure type rhinitis therapeutic device according to claim 9, wherein said second acupressure member is deposited on a sliding support frame and is connected to said pivotable piece via said sliding support frame, and further a stopper which forwardly projects from a lower edge of said pivotable piece.

11. An acupressure type rhinitis therapeutic device according to claim 10, wherein a lead wire is led from said first acupressure member directly into said front bar, while a lead wire is led from said second acupressure member via a top of said rivet pin to inside of said front bar.

12. An acupressure type rhinitis therapeutic device according to claim 11, wherein said sliding support frame has a channel-shaped sliding rail engaging with said pivotable piece on a right upper portion thereof and a channel-shaped sliding rail on a left upper portion thereof.

13. An acupressure type rhinitis therapeutic device according to claim 12, wherein said sliding rails have projections on upper edges thereof, respectively which project toward a center of said pivotable piece.

14. An acupressure type rhinitis therapeutic device according to claim 7, wherein said front bar has a projection which projects upwardly from said center thereof, and a pair of projections which project downwardly and diagonally in said opposite directions from said center thereof.

15. An acupressure type rhinitis therapeutic device according to claim 14, wherein said respective projections have said three acupressure members in a reverse side thereof, which correspond to said first acupressure point and said second acupressure points, respectively.

16. An acupressure type rhinitis therapeutic device according to claim 15, wherein said first acupressure member includes an acupressure member made of an electric insulator, and a coil spring.

17. An acupressure type rhinitis therapeutic device according to claim 16, wherein said acupressure member has a heating unit on a lower portion thereof, and a round support rod upwardly projecting from a center of an upper surface of said heating unit, and further an engaging ball is provided at said top of said support rod.

18. An acupressure type rhinitis therapeutic device according to claim 17, wherein a felt is fitted into a bottom portion of said heating unit, and a predetermined interval is kept between a ceramic heater and said felt by said electric insulator of which said heating unit is made.

19. An acupressure type rhinitis therapeutic device according to claim 18, wherein said coil spring is provided between said projection and said heating unit around said support rod to push out said felt of said acupressure member.

20. An acupressure type rhinitis therapeutic device according to claim 17, wherein a lead wire runs from a ceramic heater through said support rod and said engaging ball to the outside, and on into said projection of said front bar to join with said cord, said lead wire having said elastic coil between said engaging ball and said projection.

21. An acupressure type rhinitis therapeutic device according to claim 14, wherein said projection has a hole into which said first acupressure member is inserted.

22. An acupressure type rhinitis therapeutic device according to claim 21, wherein said engaging ball is larger in diameter by a predetermined size than said hole to prevent said first acupressure member from dropping therefrom.

23. An acupressure type rhinitis therapeutic device according to claim 21, wherein said hole is larger in diameter by a predetermined size than said support rod so that said first acupressure member may flexibly tilt in accordance with a contour of a human face to accurately press said first acupressure point.

24. An acupressure type rhinitis therapeutic device for giving thermal stimulus to a first acupressure point at a center of a glabella and to a pair of second acupressure points at opposite bottom sides of a nasal bone, said acupressure type rhinitis therapeutic device comprising:
a body having a first acupressure member contactable with said first acupressure point and second acupressure members contactable with said second acupressure points; and
a means for warming said three acupressure members, said body comprising a tank for containing hot fluid therein, said acupressure members being integrally connected to an underside of said tank and projecting downwardly therefrom, said first acupressure member having a level top surface covered with a round heat transfer plate of a predetermined thickness onto which a felt is adhered, and aid second acupressure members respectively having oblique top surfaces covered with round transfer plates of a predetermined thickness onto which felts are adhered.

25. An acupressure type rhinitis therapeutic device according to claim 24, wherein said heat transfer plates are integrated with a wall of a predetermined thickness, and said second acupressure members can accurately grasp said second acupressure points at said opposite bottom sides of said nasal bone against said oblique top surfaces thereof.

26. An acupressure type rhinitis therapeutic device according to claim 24, wherein said tank includes a cylindrical filling port at a center top portion thereof which has a cap for avoiding leakage of said hot fluid.

27. An acupressure type rhinitis therapeutic device according to claim 26, wherein said cap designed for closing said filling port includes a round roof plate and a cylindrical side plate extending vertically and downwardly from said roof plate.

28. An acupressure type rhinitis therapeutic device according to claim 27, wherein a stopper ring projecting horizontally and inwardly is provided at an inside edge of said side plate, a resilient packing of a predetermined thickness is fitted between said roof plate and said stopper ring, a ring flange projects horizontally and outwardly from one edge of said filling port and a diameter of said flange is less than an inner diameter of said side plate but greater than an inner diameter of said stopper ring.

29. An acupressure type rhinitis therapeutic device according to claim 25, wherein said wall except said filling port and said heat transfer plates is covered with a heat insulator, thereby preventing said heat from leaking out therefrom.

30. An acupressure type rhinitis therapeutic device for giving thermal stimulus to a first acupressure point at a center of a glabella and to a pair of second acupressure points at opposite bottom sides of a nasal bone, said acupressure type rhinitis therapeutic device comprising:
a body having a first acupressure member contactable with said first acupressure point and second acupressure members contactable with said second acupressure points; and
a means for warming said three acupressure members, said body comprising a tank for containing hot fluid therein, said acupressure members being integrally connected to an underside of said tank and projecting downwardly therefrom, said tank including a first recess at said underside thereof, said first recess gradually deepening from a little at the rear of said first acupressure member and increasing in depth as it extends to a rear end of said tank.

31. An acupressure type rhinitis therapeutic device according to claim 30, wherein said means for warming said three acupressure members is a hot fluid contained in said tank.

32. An acupressure type rhinitis therapeutic device according to claim 30, wherein said tank includes a second recess formed at said rear end of said tank, and said recesses are continuously integrated.

33. An acupressure type rhinitis therapeutic device for giving thermal stimulus to a first acupressure point at a center of a glabella, to a pair of second acupressure points at opposite bottom sides of a nasal bone, and to a pair of third acupressure points at opposite sides of the wings of the nose, said acupressure type rhinitis therapeutic device comprising:
a body having only five acupressure members, consisting of a first acupressure member contactable with said first acupressure point, a pair of second acupressure members contactable with said second acupressure points, and a pair of third acupressure members contactable with said third acupressure points; and
a means for warming said five acupressure members.

* * * * *